United States Patent

Eickeler et al.

[11] Patent Number: 5,116,577
[45] Date of Patent: May 26, 1992

[54] TUBULAR DOSIMETER

[75] Inventors: Edgar Eickeler; Ralf Löffelholz, both of Lübeck, Fed. Rep. of Germany

[73] Assignee: Drägerwerk Aktiengesellschaft, Lübeck, Fed. Rep. of Germany

[21] Appl. No.: 490,437

[22] Filed: Mar. 8, 1990

[30] Foreign Application Priority Data

Mar. 13, 1989 [DE] Fed. Rep. of Germany ....... 3908046

[51] Int. Cl.⁵ .............................. G01N 31/22
[52] U.S. Cl. ......................... 422/58; 422/61; 422/86; 422/88; 422/101; 436/167; 436/178; 436/902
[58] Field of Search ............... 422/83, 86, 88, 56, 422/58, 61, 101, 102; 436/116, 126, 167, 178, 902

[56] References Cited

U.S. PATENT DOCUMENTS

| | | | |
|---|---|---|---|
| 3,033,655 | 5/1962 | Grosskopf | 422/86 |
| 3,112,999 | 12/1963 | Grosskopf | 422/57 |
| 3,985,017 | 10/1976 | Goldsmith | 436/116 |
| 4,692,309 | 9/1987 | Pannwitz | 422/88 X |
| 4,783,316 | 11/1988 | Pannwitz | 436/902 X |
| 4,913,882 | 4/1990 | May et al. | 422/88 X |

FOREIGN PATENT DOCUMENTS 0728081  4/1980  U.S.S.R. ............... 436/126

*Primary Examiner*—Lynn Kummert
*Attorney, Agent, or Firm*—Walter Ottesen

[57] ABSTRACT

The invention is directed to a dosimeter for detecting gaseous or aerosol substances. The dosimeter contains a collecting reagent in a tubular shell made of a membrane permeable for the substance to be detected. The dosimeter is improved so that also substances which cannot be absorbed by the collecting reagent can be made detectable. The dosimeter includes an outer shell wherein at least one additional inner shell is provided extending coaxially to the outer shell. The two shells conjointly define an intermediate space wherein a conversion reagent is accommodated for converting the substance to be detected into a conversion product. The inner shell defines an inner space wherein the collecting reagent is disposed for collecting the conversion product.

8 Claims, 1 Drawing Sheet

TUBULAR DOSIMETER

FIELD OF THE INVENTION

The invention relates to a dosimeter for detecting gaseous and aerosol substances. The dosimeter contains a collecting reagent in a tubular shell defining a membrane permeable to the substance to be detected.

BACKGROUND OF THE INVENTION

A dosimeter of the kind referred to above for detecting carbon monoxide is described in U.S. Pat. No. 3,112,999.

Tubular dosimeters having a layer in the form of a tubular shell permeable to the substance to be detected provide an increased detection sensitivity when compared to tubular dosimeters wherein only the end of the tube is permeable to the substance to be detected. This increased detection sensitivity of tubular dosimeters is provided because the substance to be detected is provided with a far greater pass-through surface to the collecting reagent.

The known dosimeters, however, have the disadvantage that only such substances to be detected can be collected which can be absorbed directly at the collecting reagent or otherwise go into a bonding reaction. The detection of other substances which is likewise desirable is not possible with the known dosimeter.

SUMMARY OF THE INVENTION

It is an object of the invention to provide a dosimeter of the kind above which is improved so that also substances are detectable which are not taken up by the collecting reagent.

The dosimeter of the invention detects a gaseous or aerosol substance. This dosimeter includes: a tubular outer shell membrane permeable to the substance to be detected and defining a longitudinal axis; at least one inner shell disposed within the outer shell so as to extend coaxially therewith; the inner and outer shells conjointly defining an intermediate space therebetween; a conversion reagent disposed in the intermediate space for reacting with the substance to be detected to yield a conversion product; the inner shell defining an inner space; and, a collecting reagent disposed in the inner space for collecting the conversion product.

With the dosimeter of the invention, the advantages of a tubular dosimeter are made available also for such substances which are not directly detectable by the collecting reagent. In this way, the area of use of the known dosimeter is expanded to new substances which were not previously detectable. For example, the measurement of nitrogen monoxide can be carried out with the aid of a conversion reagent in an advantageous manner. This conversion reagent converts the nitrogen monoxide to nitrogen dioxide. This conversion takes palace, for example, by providing chromium(VI)oxide as an oxidizing agent. The nitrogen dioxide which is then formed is absorbed by a collecting layer of a granular collecting reagent impregnated with triethanolamine and 25% glycerol. For detecting vinyl chloride, the oxidizing agent can be used for converting into hydrogen chloride with the inner shell accommodating the collecting reagent. The collecting reagent is in the form of a granular carrier coated with sodium carbonate/triethanolamine. The collecting reagent can partially or completely fill out the inner space of the inner shell or it can be applied to the inner side of the inner shell as a layer.

According to a feature of the invention, the inner shell is held at a uniform spacing with respect to the outer shell by supports which extend substantially radially. With this arrangement, the quantity of the conversion reagent can be matched to the quantity of the collecting reagent and be distributed as uniform as possible along the tubular shell.

A further improvement of a multilayer tube is obtained in that the inner shell has a cross section which is essentially in the shape of a triangle. The edges of the triangle are braced against the inner surface of the outer shell. In this way, it is unnecessary to provide separate supports between the inner shell and the outer shell and a simple configuration of a double shell is obtained. This double shell makes possible a simple assembly during production because the triangularly-shaped inner shell must simply be pushed into the outer shell.

For detecting a gas/aerosol mixture, it is advantageous to provide the outer shell with pores in the order of magnitude of approximately 10 micrometers and the inner shell with pores in the order of magnitude of approximately 0.1 micrometer. In this way, the gas/aerosol-mixture is converted into a pure gas component by the outer conversion reagent in that the aerosol particles only penetrate the large-pore openings of the outer shell but cannot pass through the small-pore openings of the inner shell. In this manner, aerosols are preferably bonded to the conversion reagent and, in the collecting reagent, the gas particles diffusing through the conversion reagent are bonded.

A simple configuration of the dosimeter is made possible in that the shells are made of a sintered polyethylene powder having a grain size of 0.1 micrometer to 20 micrometers and a thickness of approximately 1.5 mm. Such shells are sufficiently stable that they can be configured so as to be self-supporting and do not require any mechanical supports.

It is advantageous for detecting nitrogen monoxide if the conversion reagent is formed of chromium(VI)oxide and if the collecting reagent is formed of triethanolamine with 25% glycerol on a carrier substrate.

For detecting vinyl chloride, it is advantageous to provide chromium(VI)oxide as the conversion reagent and a mixture of sodium carbonate and triethanolamine as the collecting reagent with these reagents being formed on a granular carrier substrate.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
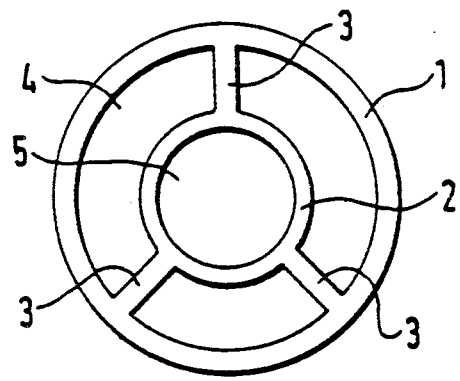
FIG. 1 is a schematic representation of a dosimeter showing the circularly-shaped shells in cross section.

A dosimeter is shown in FIG. 1 and has a circularly-shaped outer shell 1 when viewed in cross section. The outer shell is made of sintered polyethylene and an inner shell 2 likewise having a circularly-shaped cross section is disposed concentrically to the outer shell. The inner shell 2 is held in spaced relationship to the outer shell 1 by three supports 3 with the supports being spaced 120° one from the other. The supports 3 are likewise made of sintered polyethylene of the same grain size as the shells (1, 2). The supports 3 subdivide the intermediate space 4 lying between the outer shell 1 and the inner shell 2 into three like component spaces. The component spaces are each filled with a conversion reagent (not shown). The inner space 5 of the inner shell 2 accommodates the collecting reagent (not shown).

Figure 2:
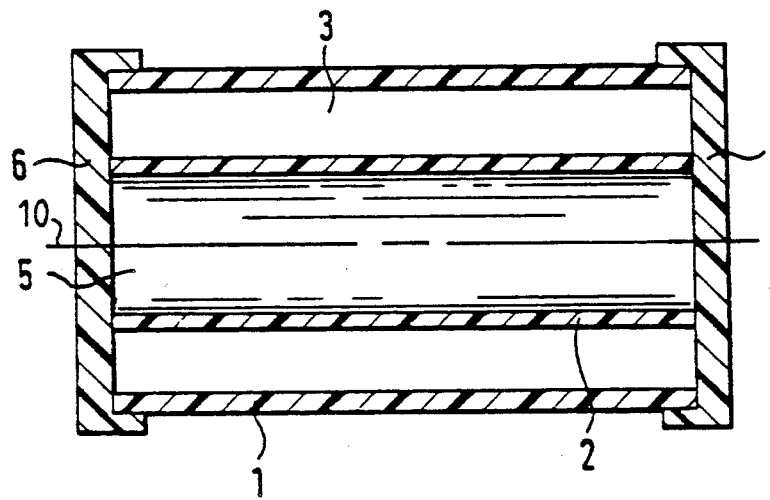
FIG. 2 is a longitudinal section taken through a dosimeter wherein the shells have a circularly-shaped cross section; and, FIG. 3 is a dosimeter according to another embodiment of the invention wherein the inner shell has a triangularly-shaped cross section.

In FIG. 2, the dosimeter of FIG. 1 is shown in longitudinal section and shows the outer shell 1 as well as the inner shell 2 and the supports 3 corresponding thereto. The shells (1, 2) define a longitudinal axis 10 and are open at their end faces and after being filled with the conversion reagent and the collecting reagent, the shells (1, 2) are closed by two end caps 6.

Figure 3:
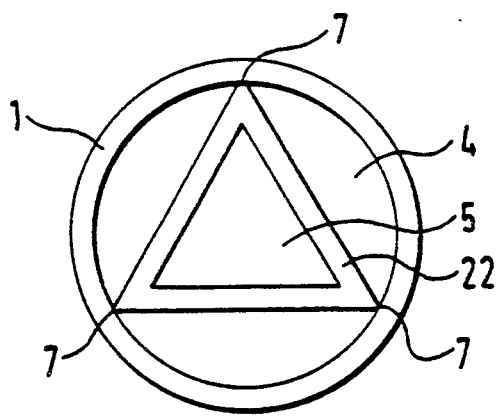

In FIG. 3, the outer shell 1 encloses an inner shell 22 having a triangular shape when viewed in cross section. The inner shell 22 has edges 7 which are in contact engagement with the inner surface of the outer shell 1.

It is understood that the foregoing description is that of the preferred embodiments of the invention and that various changes and modifications may be made thereto without departing from the spirit and scope of the invention as defined in the appended claims.

What is claimed is:

1. A dosimeter for detecting a gaseous or aerosol substance in the ambient, the dosimeter comprising:
   a tubular outer shell membrane defining a longitudinal axis;
   at least one inner shell disposed within said outer shell membrane so as to extend coaxially therewith;
   said outer shell membrane and said at least one inner shell each having first and second longitudinal ends;
   said at least one inner shell and said outer shell membrane conjointly defining an intermediate space therebetween;
   said outer shell membrane being permeable to the substance to be detected and defining a diffusion path from the ambient into said intermediate space in a direction transverse to said axis thereby facilitating the diffusion of the substance through said outer shell membrane into said intermediate space;
   a conversion reagent disposed in said intermediate space for reacting with the substance to yield a conversion product;
   said inner shell being permeable to said conversion product and defining an inner space into which said conversion product passes after diffusing through said inner shell also in a direction transverse to said axis; and,
   a collecting reagent disposed in said inner space for reacting with the conversion product.

2. The dosimeter of claim 1, the dosimeter further comprising a plurality of supports disposed in said intermediate space for holding said at least one inner shell and said outer shell membrane at a uniform spacing relative to each other.

3. The dosimeter of claim 2, said plurality of supports extending substantially radially between said shells.

4. The dosimeter of claim 1, said outer shell membrane having an inner wall surface facing said inner shell; and, said at least one inner shell having a triangular cross section and defining three edges in contact engagement with said inner wall surface so as to subdivide said intermediate space into three intermediate component spaces.

5. The dosimeter of claim 1, wherein the substance to be detected is a gas/aerosol mixture, said outer shell membrane having pores in the order of magnitude of 10 micrometers and said at least one inner shell having pores in the order of magnitude of 0.1 micrometer.

6. The dosimeter of claim 1, said at least one inner shell and said outer shell membrane being mad of sintered polyethylene powder having a grain size in the range of 0.1 to 20 micrometers and having a thickness of approximately 1.5 mm.

7. The dosimeter of claim 1, wherein the substance to be detected is nitrogen monoxide; said conversion reagent being formed of chromium (VI)oxide on a granular carrier substrate and said collecting reagent being formed of triethanolamine in solution of 25% glycerol also on a granular carrier substrate.

8. The dosimeter of claim 1, wherein the substance to be detected is vinyl chloride; said conversion reagent being formed of chromium(VI)oxide on a granular substrate and said collecting reagent being formed of a mixture of sodium carbonate and triethanolamine also on a granular carrier substrate.

* * * * *